United States Patent
Atmaca et al.

(10) Patent No.: US 10,660,744 B2
(45) Date of Patent: May 26, 2020

(54) ANCILLARY FOR THE STORAGE AND THE INJECTION OF INTRA OCULAR LENS

(71) Applicant: VSY BIYOTEKNOLOJI VE ILAC SANAYI ANONIM SIRKETI, Istanbul (TR)

(72) Inventors: Serkan Atmaca, Istanbul (TR); Pascal Bernard, Nieul sur Mer (FR)

(73) Assignee: VSY BIYOTEKNOLOJI VE ILAC SANAYI ANONIM SIRKETI, Istanbul (TR)

(*) Notice: Subject to any disclaimer, the term of this patent is extended or adjusted under 35 U.S.C. 154(b) by 251 days.

(21) Appl. No.: 15/760,731

(22) PCT Filed: Sep. 9, 2016

(86) PCT No.: PCT/TR2016/050344
§ 371 (c)(1),
(2) Date: Mar. 16, 2018

(87) PCT Pub. No.: WO2017/048211
PCT Pub. Date: Mar. 23, 2017

(65) Prior Publication Data
US 2018/0263762 A1    Sep. 20, 2018

(30) Foreign Application Priority Data
Sep. 16, 2015    (TR) .............................. 2015/11576

(51) Int. Cl.
*A61F 2/16* (2006.01)

(52) U.S. Cl.
CPC ............ *A61F 2/1678* (2013.01); *A61F 2/167* (2013.01); *A61F 2250/009* (2013.01)

(58) Field of Classification Search
CPC .............................. A61F 2/1678; A61F 2/167
See application file for complete search history.

(56) References Cited

U.S. PATENT DOCUMENTS 5,474,562 A * 12/1995 Orchowski ........... A61F 2/1664
606/107

FOREIGN PATENT DOCUMENTS

| DE | 202005009089 U1 | 8/2005 |
| DE | 102013105185 A1 | 11/2014 |
| EP | 1795154 A1 | 6/2007 |
| WO | 2010028873 A1 | 3/2010 |
| WO | 2015075489 A2 | 5/2015 |
| WO | 2015125905 A1 | 8/2015 |

* cited by examiner

Primary Examiner — Richard G Louis
(74) Attorney, Agent, or Firm — Bayramoglu Law Offices LLC

(57) ABSTRACT

This invention is related to a cartridge Injector System developed to be used for intraocular lens implantation, that enables the lens injection via a microsurgical incision in the eye and basically wraps the lens (L) by holding from the edges and provides the lens implantation with this method, also related with twisting body (7) keeping the lens in a closed environment.

7 Claims, 5 Drawing Sheets

ANCILLARY FOR THE STORAGE AND THE INJECTION OF INTRA OCULAR LENS

CROSS REFERENCE TO RELATED APPLICATIONS

This application is the national phase of International Application No. PCT/TR2016/050344, filed on Sep. 9, 2016, which is based upon and claims priority to Turkish Patent Application No. 2015/11576, filed on Sep. 16, 2015, the entire contents of which are incorporated herein by reference.

TECHNICAL FIELD

This invention is related to a cartridge injector system which contains the intraocular lens used for replacement of the natural crystalline lens in medical field especially in cataract surgeries or clear lens extraction, which enables the implantation of an intraocular lens by wrapping it.

BACKGROUND

Cataract is a disorder that hinders the person's vision and that occurs as a result of transparency loss, tarnishing, opacification and clouding of the natural crystalline lens which helps to refract light to be focused on the retina. Currently, it cannot be treated with medication, but only treated with surgery. During cataract surgery, lens which has lost its transparency is taken out and instead intraocular lens made of foldable polymer is injected. Lens injection process is performed with cartridge injector system. In current system, cartridge injector systems are used for lenses made of hydrophilic or hydrophobic materials.

Lens fitted in the cartridge is maintained in an unfolded state, natural state and then is injected through an incision in the cornea in a wrapped state. Currently, this incision size varies between 1.8 to 2.8 mm preferentially less or equal to 2.2 mm. In some cartridge-injectors lens could be deformed partially wedged between the jaws of the cartridge, and dislocated during wrapping.

In some cartridge-injector systems the lens is not protected from the external environment and can at that time be contaminated by unwanted materials or microorganism. Implantation of contaminated lens can lead infection or inflammatory reaction of the eye and could lead a potential impairment of vision of the patient and in some cases loss of the eye.

SUMMARY

The purpose of this invention is to realize a disposable cartridge injector system that maintains the lens to use in cataract surgeries and that enables the implantation of the lens into the eye.

Another purpose of the invention is to realize a cartridge injector system that wraps the lens to be used and enables the implantation of the wrapped lens into the eye through from 1.8 to 2.8 mm incision size.

Another purpose of the invention is to realize a cartridge injector system that can be used for both hydrophilic and hydrophobic lenses.

Another purpose of this invention is to realize a cartridge injector system that decreases the contamination risk by keeping the lens in closed environment and preventing any contact with external environment.

The purpose of this invention is to realize a cartridge injector system that maintains the intraocular lens stabilized with jaws to avoid risk of mispositioning in the cartridge injector set.

BRIEF DESCRIPTION OF THE DRAWINGS

In order to fulfill the purpose of this invention, a cartridge injector system is illustrated in the attached drawings and this figure.

Figure 1:
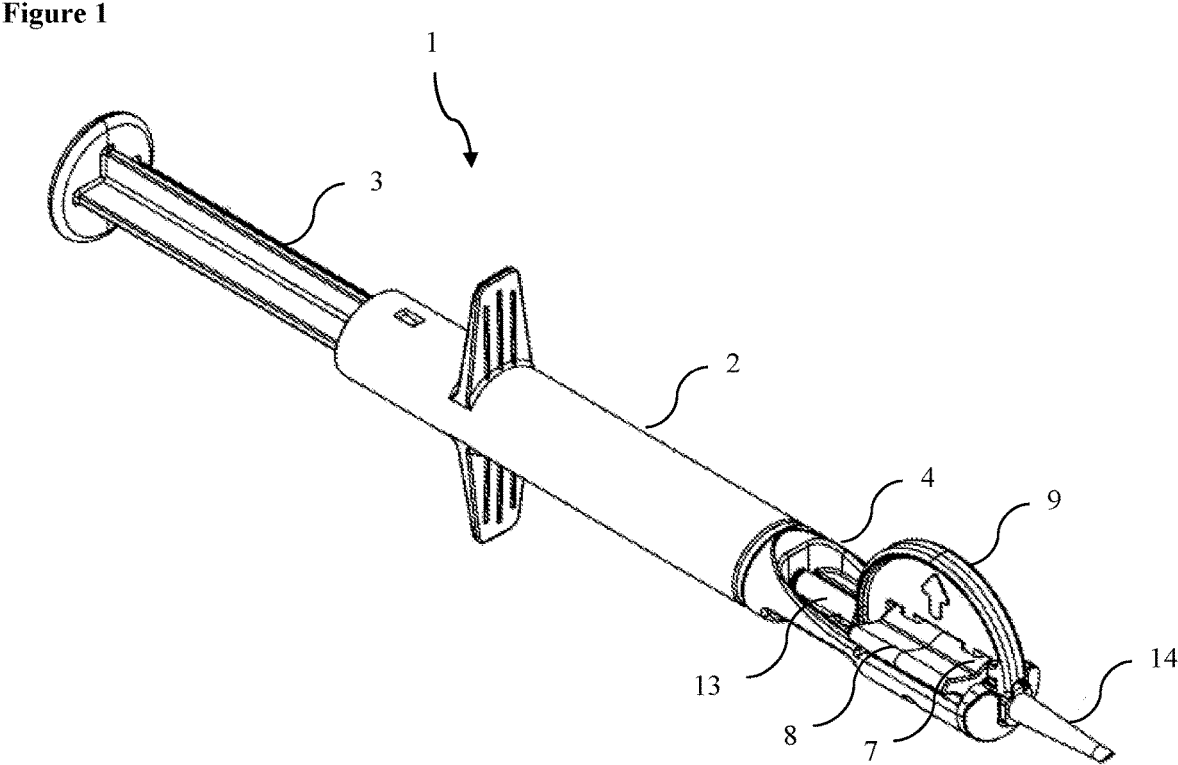
FIG. 1. is the view of the present invention cartridge injector system.
Figure 2:
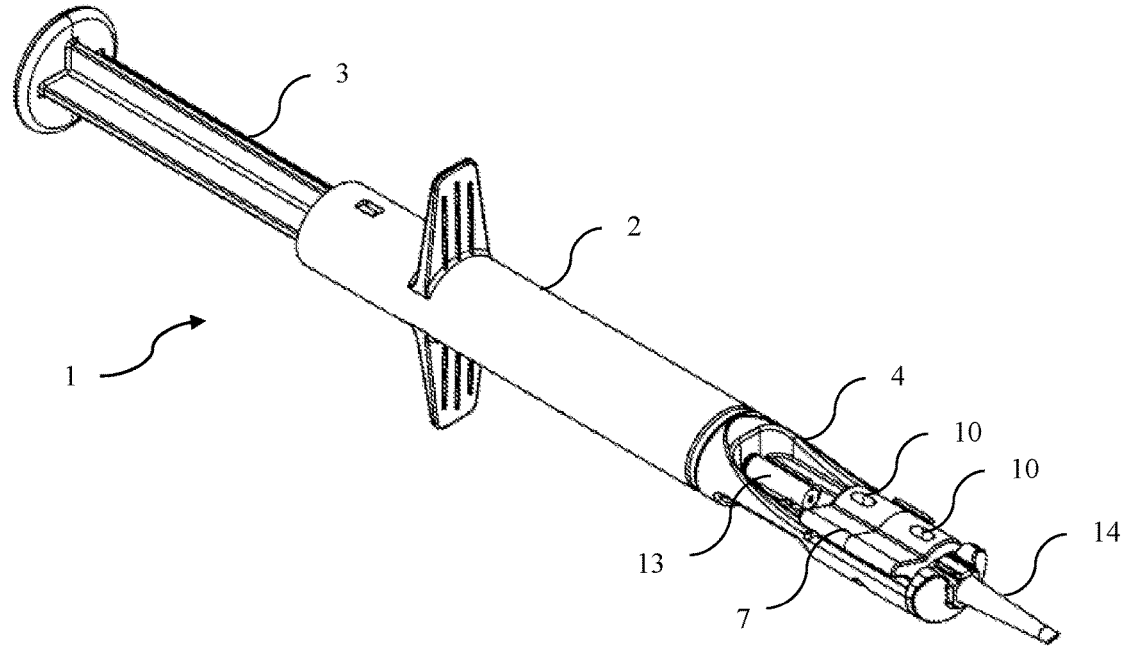
FIG. 2. is the state of present invention cartridge injector system with removed safety locking part.

Parts shown in figure are individually numbered and their numbers are given below.
1. Cartridge Injector System
2. Primary Body
3. Plunger
4. Secondary Body
5. Spring
6. Jaw
7. Body
8. Lever
9. Safety locking Part
10. Hole
11. Primary Extension
12. Secondary Extension
13. Cushion
14. Cartridge
L. Lens
K. Cartridge Kit

DETAILED DESCRIPTION

Present invention cartridge injector system (1) essentially comprising,
   One primary body (2) in the form of a hollow cylinder,
   One secondary body (4) having lower diameter than the primary body (2) and having the shape of an empty crescent with open top in order to assemble the system parts.
   One plunger (3) enabling the passage of the lens (L) through primary body (2) and cartridge channel with compressive force applied upon.
   One spring (5) pushing out the lens (L) while being squeezed under the compressive force applied upon the plunger (3),
   Two jaws (6) holding the lens (L) from its two edges with involuted ends, releasing it in open state and wrapping it in closed state,
   A body (7) maintaining the lens (L), enabling the closing of the jaws (6) due to its internal geometry and providing wrapping of the lens (L) when turned, One lever (8) in the form of an extension connected to the body (7) serving as a holder for easy turning of the body (7), A safety locking part (9) preventing any movement of the lever (8) and thus the body (7) before the desired time.

Two holes (10) through which the safety locking part (9) is assembled on the body (7), having different and gradually decreasing diameter values and when the safety locking part (9) is removed viscoelastic fluid can be injected through, One extension (11) being attached to the hole (10) on the body (7), having two different gradually decreasing diameter values, One secondary extension (12) being attached to the hole on the secondary body (4) and immobilizing the safety handle (9), One cushion transmits the compression force by squeezing without damaging the lens (L) exerted on plunger (3) and being transmitted to the spring (5), One cartridge (14) presenting 2 hinges to come to a close hollow tube, Present invention cartridge injector system (1) is a system that maintains the intraocular lens and enables its implantation into the eye. The intraocular lens (L) is wrapped in the cartridge injector system (1) and the wrapped lens (L) is implanted into the eye through 1.8-2.8 mm incision size that is made on the patient eye during cataract surgery.

In the present invention cartridge injector system (1), the body comprises of a primary body (2) and a secondary body (4). These two body parts could be attached to each other or could be comprised of one piece. Plunger (3) with the cushion (13) attached enters the hollow primary body (2) in the shape of a cylinder and transfers the compression force exerted on itself to a spring (5) located in secondary body (4). Secondary body (4) has smaller diameter than primary body (2) and wall height decreases gradually to the tip and it is transformed into the shape of a crescent. Top part of the secondary body (4) is open and it allows the assembly of system parts. In one embodiment of the invention, body (7) and a cushion are assembled on the secondary body (4), a safety locking part (9) is attached to the body (7). The top of this secondary body (4) is open in order to interfere manually and externally in assembled parts. Upper portion surface of the secondary body (4) where the parts are assembled is also gradual. The upper portion where cushion (13) is assembled is positioned higher than the surface where the body (7) is assembled (FIG. 1-2-3-8).

In one embodiment of invention, body (7) is shaped like an eccentric hollow body.

In one embodiment of the invention, side wall of the secondary body (4) has smaller height value than the other walls in the direction where a lever (8) stands before turning, it allows the placement of the lever (8). Side wall where lever is pointed has small height value along its length and it is not in contact with the lever (8).

In one embodiment of the invention, there are jaws shaped holders in order to apply a constant force on the plunger (3) by placing the user's fingers on the primary body (2). These holders are placed on the primary body (2) with right angle. On the holders, there are rims parallel to the holder surface to prevent the fingers from slipping. These holders are extensions coming out from primary body (2). In a preferred embodiment of the invention, desired brand and/or description can be written on the primary body (2).

In a preferred embodiment of the invention, the spring (5) that the plunger (3) transmits the compression force on is in the form of spiral spring.

When the present invention cartridge injector system (1) is desired to be used firstly the safety locking part (9) should be removed from the body (7). There are two different extensions on the safety locking part (9). Primary extension (11) has two different diameter values and it is attached on a hole (10) with gradual diameter values on the body (7). Diameter values of primary extension (11) and grade and diameter values of the hole (9) need to be proportional to each other in order to perform stabilizing operation. On the primary extension (11), tip diameter is smaller than the part coming out of the safety locking part (9) (FIG. 4).

Figure 4:
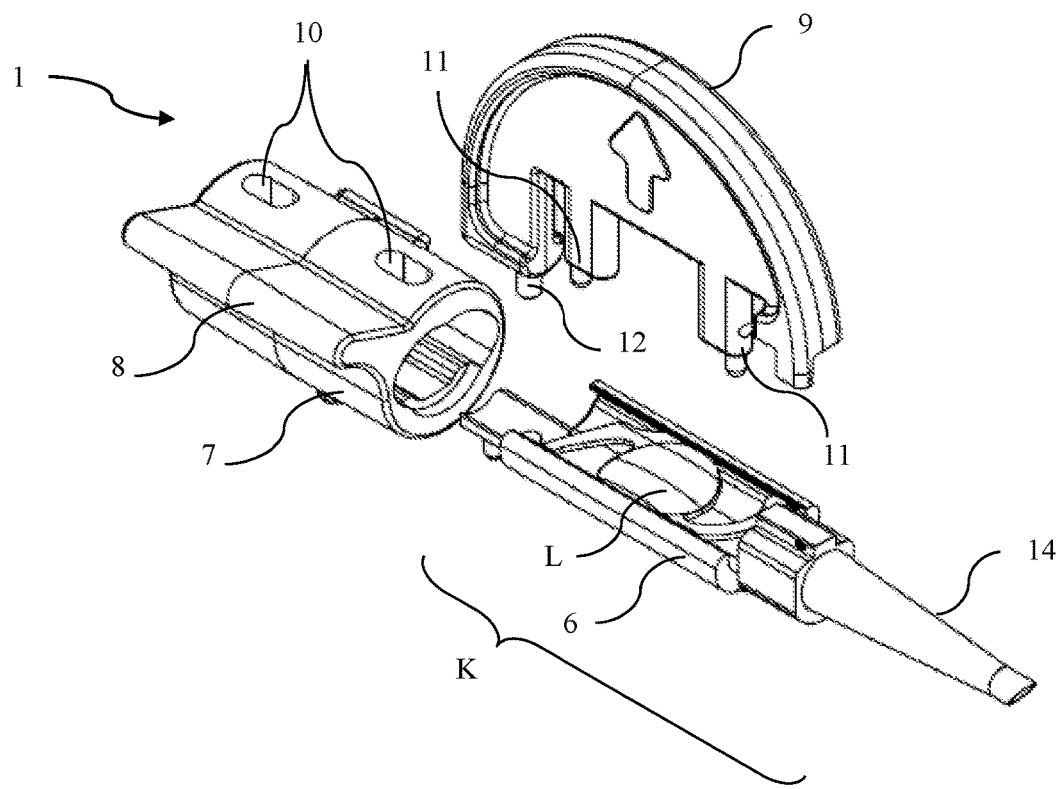
FIG. 4. is the exploded view of the cartridge kit.
Figure 5:
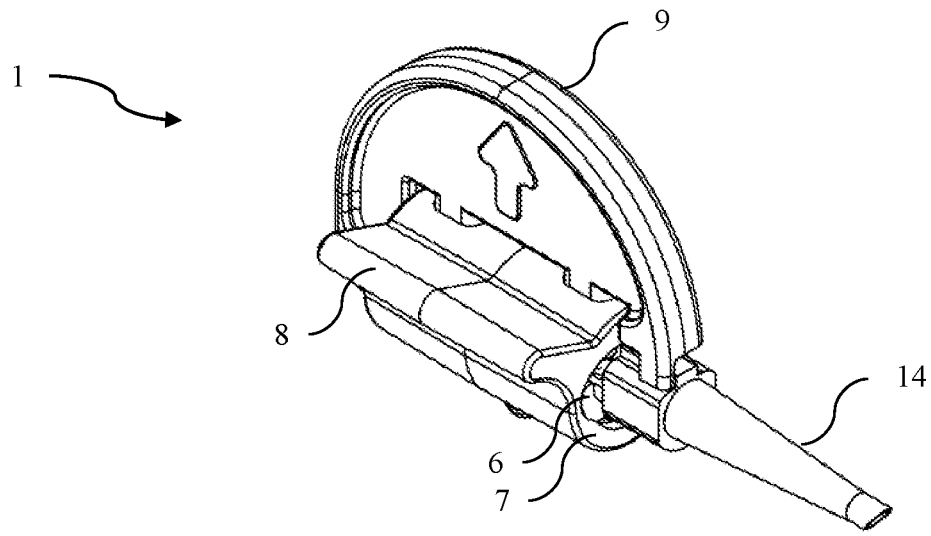
FIG. 5. is the view of cartridge kit.

A Secondary extension (12) is coming out of the safety locking part (9) and is attached to the hole on the secondary body (4) (FIG. 4).

In a preferred embodiment of the invention, the hole (10) on the body (7) is a gradual hole with 2 different diameter values. Primary extension (11) is attached to this hole (10). The diameter of the hole (10) which is closer to the body (7) surface is bigger than the inside diameter. In an embodiment of the invention, the hole diameter (10) decreases from larger to smaller hole.

The hole (10) is exposed with the removal of the safety locking part (9). From this hole (10), viscoelastic fluid is injected in the body (7) with a syringe. Viscoelastic fluid enables the lens (L) to slide, protect the surfaces of the intraocular lens and pass easily through the cartridge (14) and ease its implantation into the eye. Said cartridge (14) that the wrapped lens (L) is injected through.

Figure 3:
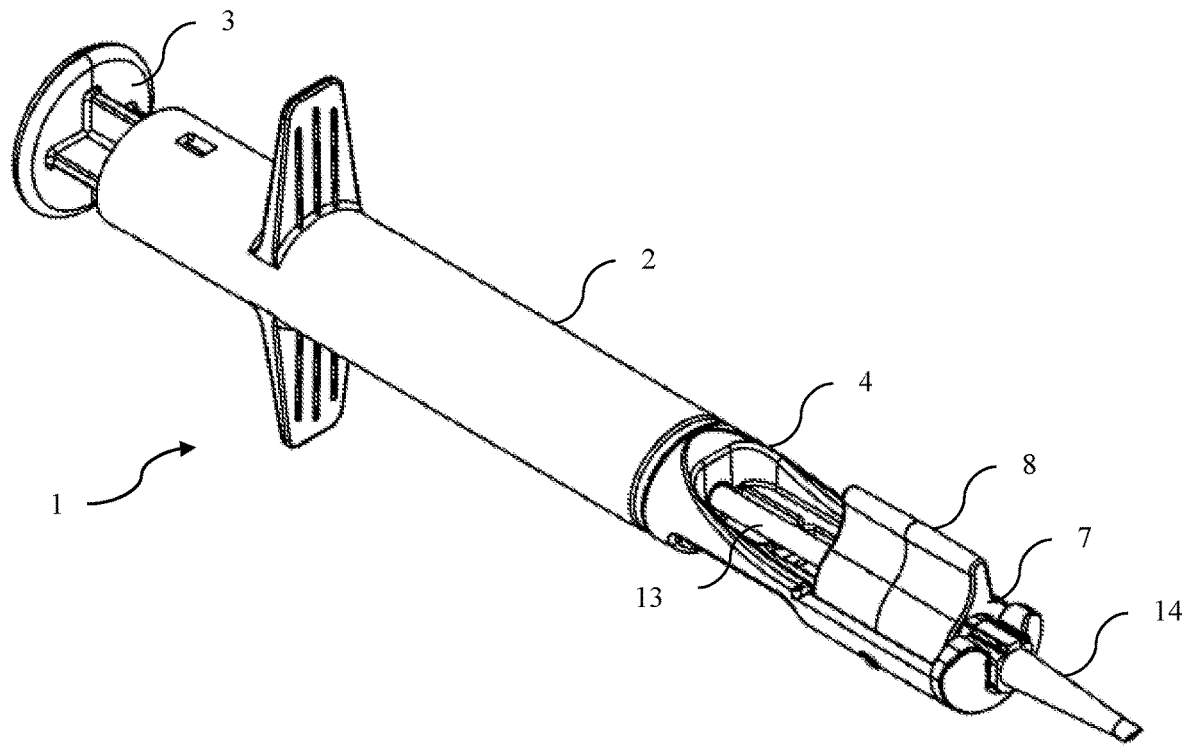
FIG. 3. is the view of turning of the body to the predetermined direction in order to wrap the lens.

When safety locking part (9) is removed, the lever (8) is released and it can be turned toward a predetermined direction. In an embodiment of the invention body (7) and lever (8) are turned towards the predetermined direction under force that user applies manually. Lever (8) is designed as a holder in order to enable for user to perform the turning operation easily (FIG. 3-4).

In a preferred embodiment of the invention, there are bumps on the lever (8) to prevent the slipping of the user's fingers, the firm holding and turning of the lever (8). These bumps are aligned parallelly to secondary body (4) on the outer surface of the lever (8).

Figure 6:
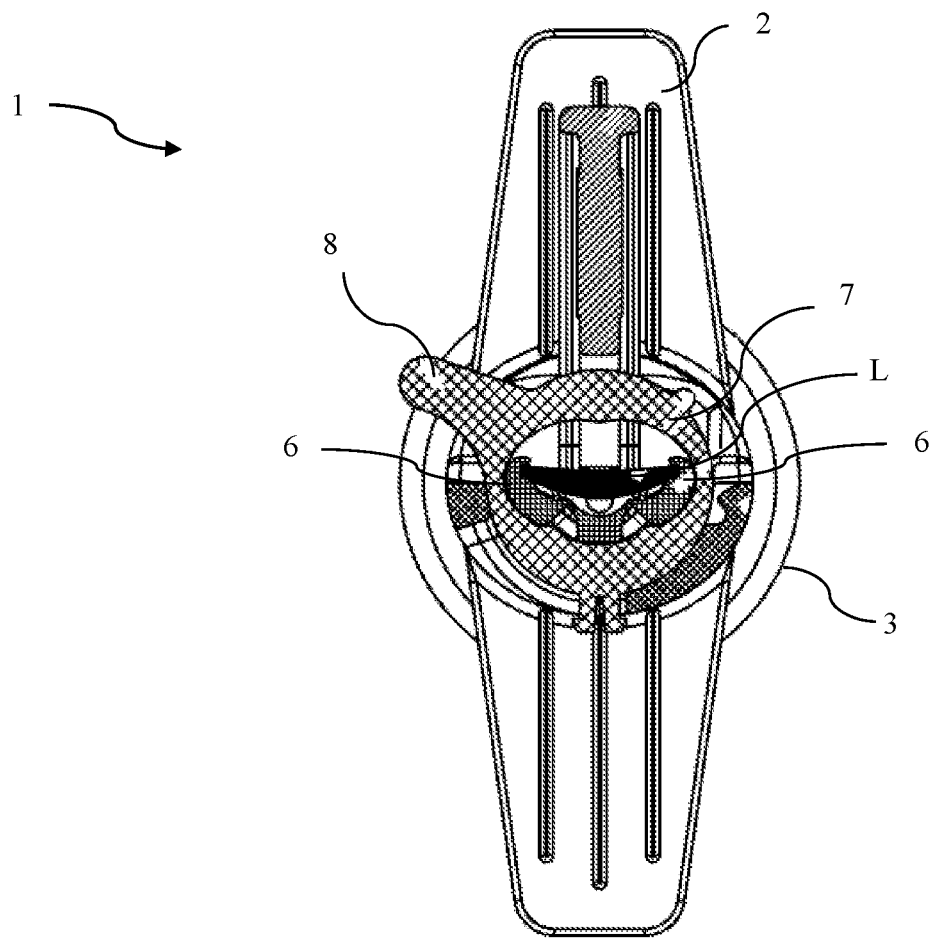
FIG. 6. is the frontal sectional view of the cartridge injector with lens in unfolded state.
Figure 7:
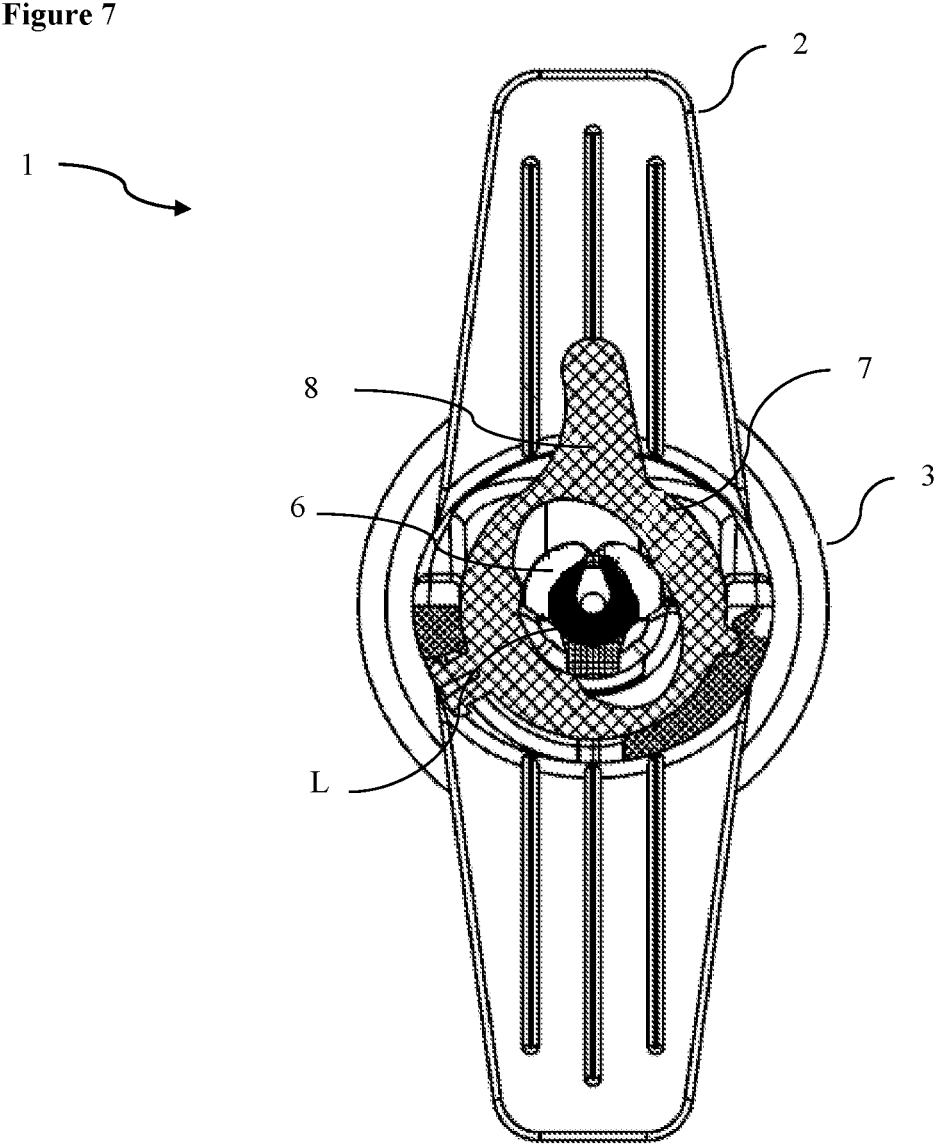
FIG. 7. is the frontal sectional view of the cartridge injector with lens in folded state by moving the turning extension.
Figure 8:
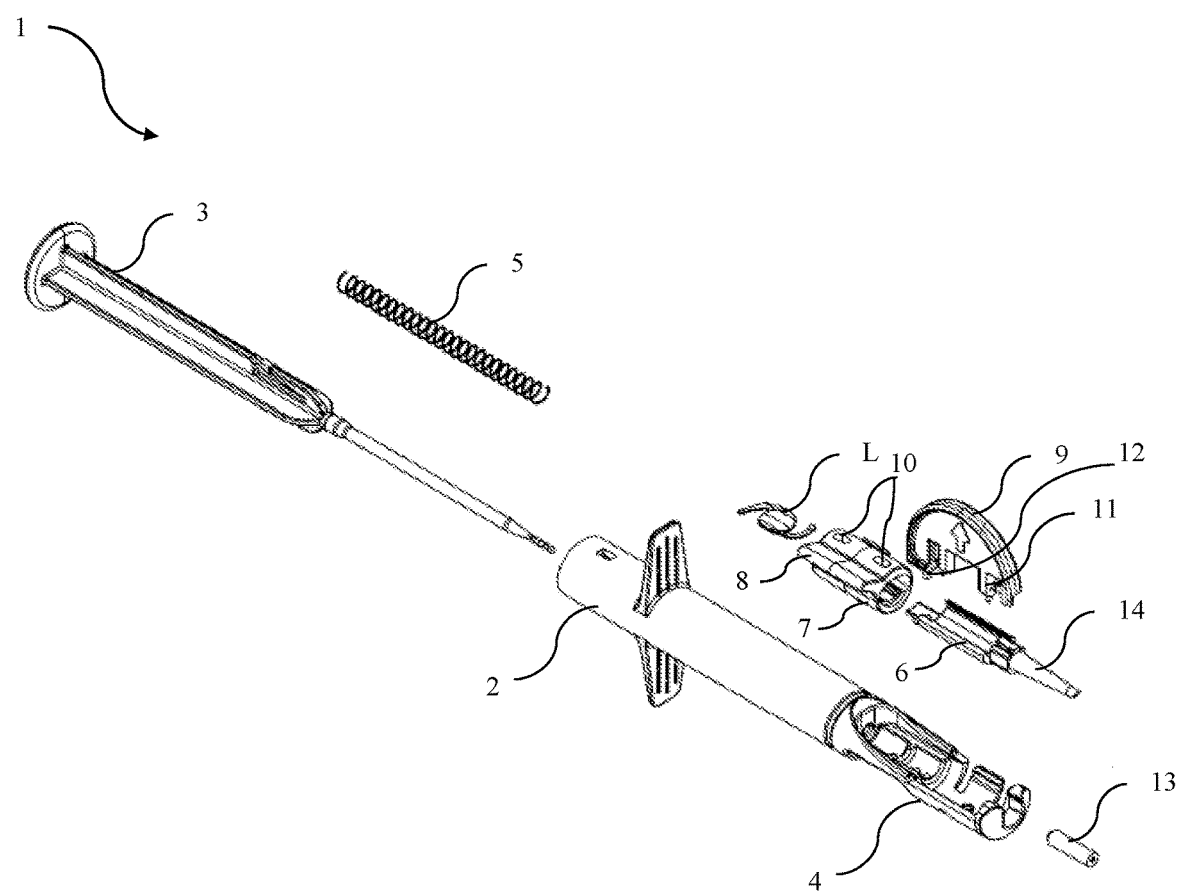
FIG. 8. is the exploded view of the cartridge injector system.

Lever (8) is turned by the applied force and it turns the body (7) also. Two jaws (6) are located in the body (7). The outer surface of these jaws (6) and the inner surface of the body (7) are in contact. Thus, movement of the body (7) is transmitted to the jaws (6). This turning motion is carried out by geometrical shape of the inner surface of the body (7). In an embodiment of the invention there is an empty space in elliptical shape inside the body (7). The bottom half of this elliptical shape located near the secondary body (4) has 3 different spring geometries. Spring geometry which is located in body (7), which forms inner walls with different slopes and angles dislocates under the influence of turning motion and this dislocation causes closure of the jaws (6) (FIG. 6-7).

When the body (7) is unconstrained, inner elliptic geometry is in the form of horizontal ellipse. Accordingly, inner elliptic geometries occupy wide spaces in horizontal and jaws (6) are spread over this geometry. With the turning motion, inner elliptic geometry becomes vertical and the area in which the jaws (6) are located becomes narrower. Narrowed space forces the jaws (6) to close and consequently the lens to fold. Tip of the jaws (6) are curved inward in order to hold both ends of the lens (L) (FIG. 6-7).

When the jaws (6) are in open state, lens (L) is held without constraint in vertical. When the jaws (6) are closed, lens (L) is wrapped while held by its two ends. In an embodiment of the invention, when the jaws (6) are closed and the lens is wrapped, lever (8) stands at a right angle to secondary body (4).

The inner surface of the jaws (6) is composed of gradually sloping walls. In a preferred embodiment of the invention, tips of the jaws (6) are bent inward and hold the lens (L) from its ends. Surface of the held lens (L) is in contact with a first stage of the jaw. After the first stage, there is a second stage which has larger radius. Difference in diameter ensures the lens (L) not being crushed by the jaws (6) when the lens is wrapped. The end parts of the lens (L) are being held with the tips bent inward on the first stage of the jaw which has narrower diameter and its dislocation is prevented. With the second stage being wider, the contact between the inner jaw (6) surface and the lens (L) is cut off, exerted external force is prevented and deformity of the lens (L) that may occur as a result of crushing is prevented.

After wrapping of the lens (L) by moving the body (7), user applies compression force on the plunger (3). Compression force is being transmitted to the spring (5), the spring (5) squeezes cushion (13). Squeezed cushion (13) pushes the wrapped lens (L) to make it get out by passing it through the cartridge (14). Damage that compression force may inflict on the lens (L) is prevented as the lens (L) is not in direct contact with the spring (5). Cushion (13) that enables the motion transmission in between transmits the compression force by squeezing without damaging the lens (L). In one embodiment, cushion (13) made of Silicon or Thermoplastic elastomer.

In one embodiment, cartridge (14) presenting 2 hinges that has different lengths to come to a close hollow tube with inclined outer surface.

On the tip of the secondary body (4) a cartridge (14) is attached. In a preferred embodiment of the invention 1.59 mm cartridge tip diameter can be used in 1.8-2.8 mm incision gap. It depends on the surgery technic used. 1.8 incision size corresponds to a wound assisted implantation.

The lens (L) in a closed system is protected from external factors inside the body (7) thus reducing the risk of further adverse event as infection of the eye. Also with the inner surface of the body (7) which has different gradual angle and slopes in elliptic shape, the lens (L) is wrapped safely.

Hydrophilic lenses (L) are the lenses that are kept in water or saline before implantation. Hydrophobic lenses are delivered in a dry state.

Hydrophilic lenses (L) are kept in liquid in its special packaging called cartridge kit (K) with body (7), safety locking part (9) and cartridge (14) in which the lens (L) is found in ready state. During operation, cartridge kit (K) is taken out of the container, is attached to the secondary body (4) and is used. With hydrophobic lenses (L), there is no need for the cartridge kit (K) to be conserved separately. Due to the detachable feature of the cartridge kit (K), mentioned cartridge injector system (1) can be used with both hydrophobic lenses (L) and hydrophilic lenses (L).

The invention claimed is:

1. A cartridge injector system used for medical purpose especially in cataract surgeries, comprising: a primary body in the form of a hollow cylinder and the primary body has holders providing holding, a plunger passing through the primary body under a compression force applied and enables a lens to go out, a spring regulating the exit of the lens while being squeezed under the compression force applied upon the plunger, a cushion provided between the lens and the plunger, wherein the cushion transmits the compression force exerted on the plunger and being transmitted to the spring, without damaging the lens; a secondary body attached at a distal end of the primary body and having a first diameter smaller than a second diameter of the primary body and having a shape of an empty crescent with an open top in order to assemble system parts; a rotational body shaped like an eccentric hollow body; two jaws located in the rotational body and holding the lens from two edges with involuted ends, releasing the lens in an open state and wrapping the lens in a closed state, wherein the rotational body enables the jaws to close due to an internal geometry of the rotational body and wraps the lens, when turned causing the jaws to close; a lever in form of an extension connected to the rotational body serving as a holder for the rotational body, a safety locking part preventing movement of the lever and the rotational body before a desired time and maintaining the lens always in a same longitudinal position during storage, two holes provided in the rotational body, wherein the safety locking part is assembled on the rotational body, wherein the two holes have different and gradually decreasing diameter values and when the safety locking part is removed a viscoelastic fluid can be injected through the two holes, a first extension on the safety locking part being attached to the two holes on the rotational body, secondary a second extension on the safety locking part attached to a hole on the secondary body for immobilizing the safety locking part, a cartridge comprising a cartridge channel and two hinges, wherein the cartridge forms a close hollow tube forming the cartridge channel with an inclined outer surface, the cartridge being attached to a distal end of the rotational body.

2. The cartridge injector system according to claim 1, wherein, the secondary body is in the form of a pit along a button length of the sidewall where the lever stands without constraint.

3. The cartridge injector system according to claim 1, wherein the lever extensions in parallel to the secondary body.

4. The cartridge injector system according to claim 1, wherein the rotational body opens the jaws, wherein the jaws are in contact with an inner surface of the rotational body, the inner surface of the rotational body is in form of a horizontal ellipse when unconstrained and a vertical ellipse when turned.

5. The cartridge injector system according to claim 1, wherein the jaws hold the lens freely in a horizontal surface when open and holds the lens from ends when closed.

6. The cartridge injector system according to claim 1, wherein the jaws have tips bended inward in order to hold the lens and an inner surface of the jaws has different stages of geometry.

7. The cartridge injector system according to claim 1, wherein the lens is a hydrophilic lens or a hydrophobic lenses.

* * * * *